US00PP34133P2

(12) United States Plant Patent
Bacon et al.

(10) Patent No.: US PP34,133 P2
(45) Date of Patent: Apr. 19, 2022

(54) PLUM TREE NAMED 'SUPLUM63'

(50) Latin Name: *Prunus salicina*
Varietal Denomination: Suplum63

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 17/540,588

(22) Filed: Dec. 2, 2021

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472
See application file for complete search history.

*Primary Examiner* — Anne Marie Grunberg
(74) *Attorney, Agent, or Firm* — Knobbe, Martens, Olson & Bear, LLP

(57) ABSTRACT

The new variety of plum tree 'Suplum63' is characterized by a semi-upright habit, and by having fruit that is very large for a late season plum, with black skin, dark red firm flesh, a mildly sweet flavor, and a stone that is adherent to the flesh.

1 Drawing Sheet

Latin name of the genus and species claimed: *Prunus salicina.*

Variety denomination: 'SUPLUM63'.

BACKGROUND AND SUMMARY OF THE INVENTION

This application relates to the discovery and asexual propagation of a new and distinct variety of plum tree, *Prunus salicina* 'Suplum63'. The new variety was first originated by hybridization near Wasco, Kern County, Calif. and identified in September 2016 by Terry A. Bacon and Terrence J. Frett as breeder number 'PL1972RB'.

The seed parent is 'Suplumfiftysix' (U.S. Plant Pat. No. 31,078), and the pollen parent is 'PL1396RB' (unpatented breeding selection). The parent varieties were first crossed in March 2013, the date of first sowing being March 2014 and the date of first flowering being March 2016. The new plum variety 'Suplum63' was first asexually propagated by Terry A. Bacon and Terrence J. Frett near Wasco, Kern County, Calif. in December 2016 by dormant grafting.

The new variety 'Suplum63' is a semi-upright tree characterized by having fruit that is very large for a late season plum, with black skin, dark red firm flesh, a mildly sweet flavor, and a stone that is adherent to the flesh.

The new variety 'Suplum63' is distinguished from its pollen parent, 'PL1396RB' in that the fruit has dark red flesh compared to the yellow-red flesh of 'PL1396RB'. Additionally, the fruit of the new variety ripens about 47 days earlier than the fruit of 'PL1396RB'. Further, the trees of the new variety 'Suplum63' have a semi-upright habit, while 'PL1396RB' trees have an upright habit.

The new variety 'Suplum63' resembles its seed parent 'Suplumfiftysix' (U.S. Plant Pat. No. 31,078) in that the fruit of both varieties have red flesh. However, the ripening of the fruit of the new variety 'Suplum63' starts 22 days earlier than 'Suplumfiftysix'. The new variety 'Suplum63' also has a semi-upright habit, while 'Suplumfiftysix' has an upright habit The new variety 'Suplum63' ripens late in the season like 'Suplumsix' (U.S. Plant Pat. No. 2,747). However, ripening of new variety 'Suplum63' starts 17 days earlier, on August 16 compared to September 2 for 'Suplumsix'. Further, the fruit of the new variety 'Suplum63' has dark red flesh compared to yellow flesh for 'Suplumsix'.

The new variety 'Suplum63' ripens at the same time as 'Black Kat' (U.S. Plant Pat. No. 13,134). However, the fruit of the new variety 'Suplum63' has dark red flesh compared to yellow flesh for the fruit of 'Black Kat'. Additionally, bloom starts 23 days earlier for the new variety 'Suplum63' than for 'Black Kat'.

The fruit of the new variety 'Suplum63' has red flesh like the fruit of 'Suplumeleven' (U.S. Plant Pat. No. 4,902). However, the new variety 'Suplum63' is distinguished from 'Suplumeleven' in that its fruit has dark red flesh compared to light red flesh for 'Suplumeleven'. Further, ripening of the fruit of the new variety 'Suplum63' starts about 41 days later than for 'Suplumeleven'.

The new variety 'Suplum63' has been shown to maintain its distinguishing characteristics through successive asexual propagations by, for example, cuttings and grafting.

BRIEF DESCRIPTION OF THE PHOTOGRAPH

The accompanying color photographic illustration, FIG. 1, shows typical specimens of the foliage and fruit of the plum variety 'Suplum63'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, 1986.

The descriptive matter which follows pertains to three-year-old 'Suplum63' trees grown in the vicinity of Wasco, Kern County, Calif. during 2021 and is believed to apply to plants of the variety grown under similar conditions of soil and climate elsewhere.

TREE

General: (Measurements taken on three-year-old trees unless otherwise noted).

*Size*.—Medium: reaches a height of approximately 3 meters with normal pruning.

*Habit*.—Semi-upright.

*Vigor*.—Strong. Top shoot growth of 1.5 meter during the growing season.

*Productivity*.—Very productive, about 700 25 lb cartons per acre. Fruit set is usually two or more times desired amount for marketable size fruit. Thinning and spacing of fruit is necessary.

*Bearer*.—On spurs and long shoots.

*Fertility*.—Self-incompatible; requires pollinator.

*Hardiness*.—Hardy in all fruit growing areas of California. Winter chilling requirement is approximately 400 hours at or below 7.2° C.

*Disease resistance/susceptibility*.—Under close observation in Kern County, Calif., no particular plant/fruit disease resistance/susceptibility has been observed.

*Insect resistance/susceptibility*.—Under close observation in Kern County, Calif., no particular plant/fruit insect resistance/susceptibility has been observed.

Trunk: (Measurements taken at approximately 30 cm above soil line on mature tree).

*Diameter*.—Approximately 13 cm.

*Texture*.—Medium shaggy, increasing with age of tree.

*Trunk color*.—About Medium Greyed-Green 198B with highlights of Dark Greyed-Orange 166A, becoming darker with age.

Branches: (Measurements taken at approximately 90 cm above soil line).

*Size*.—Diameter approximately 10 cm.

*Texture*.—Medium shaggy, increasing with age.

*Color*.—About Dark Grey 201B with highlights of Medium Grey-Brown 199B, becoming darker with age.

*Lenticels*.—Present.

*Lenticels density*.—Plentiful, about 50/cm$^2$.

*Lenticels color*.—About Medium Greyed-Green 197C.

*Lenticels dimensions*.—Length: approximately 1-3 mm. Width: approximately 0.5 mm.

One year old shoots: (Data taken in September at mid-point of current-season growth).

*Size*.—Average diameter approximately 7 mm.

*Topside color*.—About Dark Green 139A, becoming Medium Greyed-Orange 166B by September.

*Underside color*.—About Dark Green 139A, becoming Medium Greyed-Orange 166B by September.

*Internode length*.—Approximately 1-3 cm, average 2 cm. Midway on shoot.

*Lenticels color*.—About Medium Greyed-Green 197C.

*Lenticels size*.—Very small, difficult to see, about 0.2 mm diameter.

*Lenticels density*.—Medium.

*Spur length*.—Medium, usually 8 mm.

*Anthocyanin intensity on upper side of shoot*.—Medium.

Vegetative buds:

*Position of vegetative bud in relation to shoot*.—Slightly held out.

*Size*.—Medium, approximately 1.7 mm wide×2.7 mm long.

*Shape*.—Ovoid.

*Bud shape at apex*.—Obtuse.

*Color*.—About Dark Greyed-Orange 166A.

Flower buds:

*Shape*.—Ovoid.

*Dimensions*.—Approximately 1.1 mm wide×2 mm long.

*Color*.—About Medium Greyed-Orange 177B.

*Distribution*.—2-6 buds, generally on spurs and one-year old shoots.

*Ratio of flowering buds to vegetative buds*.—2-6 flower buds to 1 vegetative bud.

FOLIAGE

Leaves: (Data taken in July on fully expanded leaves at mid-point of the current season growth).

*Average length*.—Medium; approximately 11 cm without petiole.

*Average width*.—Medium; approximately 5.5 cm.

*Length/width ratio*.—Moderately elongated; about 2:1.

*Shape*.—Elliptic.

*Color*.—Upper surface: About Dark Green 139A. Lower surface: About Medium Green 136C.

*Glossiness of upper side*.—Medium.

*Angle at apex* (*excluding tip*).—Acute.

*Shape of base*.—Acuminate.

*Vein color*.—About Light Green 139D with highlights of Medium Greyed-Orange 176C where exposed to sun.

*Venation*.—Pinnately net veined.

*Surface texture*.—Smooth on both upper and lower surfaces.

*Shape in the cross section*.—Concave.

*Profile*.—Up folded.

*Leaf blade tip*.—Curved downwardly.

*Undulation of margin*.—Slight.

*Density of pubescence of lower side*.—Absent or very sparse.

*Incisions of margin*.—Bi-crenate.

Petiole:

*Average length*.—Long, approximately 15 mm.

*Average diameter*.—Approximately 2 mm.

*Color*.—About Light Green 139D with highlights of Medium Greyed-Orange 176C where exposed to sun.

Stipules:

*Number/leaf bud*.—Usually one.

*Typical length*.—Approximately 6 mm.

*Color*.—About Dark Greyed-Orange 166A when dried.

*Persistence*.—Falls off.

Leaf glands:
*Average number and arrangement.*—2-4, alternating. Predominately on petiole and occasionally on lower leaf.
*Form.*—Globose.
*Diameter.*—Approximately 0.3 mm.
*Color.*—About Medium Greyed-Yellow 162A becoming Dark Greyed-Orange 166A over time.

FLOWERS

General:
*Time of beginning of flowering.*—Medium for the San Joaquin Valley, Calif.
*Flower blooming period.*—First bloom: Approximately February 21 in Wasco, Calif. Full bloom: Approximately February 25 in Wasco, Calif.
*Location of first bloom.*—Lower third of tree canopy.
*Location of full bloom.*—Central part of the tree canopy.
*Duration of bloom.*—Approximately 10 days.
*Flower diameter.*—Medium, approximately 25 mm.
*Flower form.*—Non-Showy.
Pedicels:
*Length.*—Long, approximately 12 mm.
*Diameter.*—Approximately 1.2 mm.
*Color.*—About Light Green 138C.
*Pubescence.*—Absent.
Petals:
*Number.*—5.
*Arrangement.*—Slightly overlapping.
*Color.*—About White 155A.
*Length.*—Medium, approximately 10 mm.
*Width.*—Approximately 7 mm.
*Shape.*—Obovate.
*Apex shape.*—Rounded.
*Base shape.*—Narrows at point of attachment.
*Surface texture.*—Smooth.
*Undulation of margins.*—Medium.
*Frequency of flowers with double petals.*—None.
*Claw.*—Absent.
Sepals:
*Number.*—5.
*Length.*—Approximately 4 mm.
*Width.*—Approximately 3 mm.
*Shape.*—Triangular.
*Color.*—About Light Green 138C.
*Surface texture.*—Smooth.
*Margins.*—Undulating.
*Positioning.*—Adpressed to petals.
*Frequency of flowers with double sepals.*—None.
Stamens:
*Number.*—About 22-28; usually 25.
*Average length.*—Variable, ranging from 3 mm to 10 mm.
*Filament color.*—About White 155A.
*Flower pollen color.*—About Light Yellow-Orange 18A.
*Position.*—Perigynous.
Pistil:
*Average length.*—Approximately 3-4 mm.
*Ovary diameter.*—Approximately 2.2 mm.
*Pubescence.*—Absent.
*Stigma extension in comparison to anthers.*—Usually below.
*Frequency of supplementary pistils.*—Rare.
Receptical:
*Depth.*—Medium, approximately 4 mm.
*Pubescence of inner surface.*—Absent.
*Pubescence of outer surface.*—Absent.

FRUIT

General: (Description taken at firm-mature near Wasco, Kern County, Calif.).
Ripening:
*Time of beginning of fruit ripening.*—Late season.
*Date of first pick.*—Approximately August 16.
*Date of last pick.*—Approximately August 26.
Size:
*Height.*—Tall, approximately 70 mm.
*Diameter in line with suture plane.*—Approximately 70 mm.
*Diameter perpendicular to suture plane.*—Broad, approximately 70 mm.
*Average weight.*—Very large, approximately 170 g.
Peduncle:
*Length of stem.*—Short, approximately 7 mm.
*Diameter of stem.*—Approximately 3 mm.
*Color of sent.*—About Light Green 139D.
Shape:
*Viewed from apex.*—Circular.
*Viewed in-line with suture.*—Circular.
*Viewed from side, perpendicular to suture.*—Circular.
*Symmetry.*—Symmetric or slightly asymmetric.
*Shape of base.*—Depressed.
*Shape of apex.*—Rounded.
Fruit stem cavity:
*Depth of stalk cavity.*—Shallow; Approximately 7 mm.
*Width of stalk cavity.*—Medium; Approximately 11 mm.
*Depth of suture.*—Absent or very shallow.
Fruit skin:
*Thickness.*—Medium, typical of most varieties.
*Flavor.*—Mildly tart.
*Adherence to flesh.*—Strong.
*Surface texture.*—Slight rippled.
*Pubescence.*—None.
*Bloom on skin.*—Medium.
*Ground color.*—Not visible.
*Overcolor.*—About fully Black 202A.
*Relative area of overcolor.*—Whole surface.
*Pattern of overcolor.*—Solid.
*Reticulation.*—Present.
*Tendency to crack.*—Rare.
*Number of lenticels.*—Medium, about 10/cm$^2$.
*Size of lenticels.*—Very small, approximately 0.2 mm.
Flesh at firm-mature harvest stage:
*Ripens.*—Evenly.
*Texture.*—Crisp-juicy.
*Flavor.*—Mildly sweet, medium acid, about 38 Brix: Acid.
*Color.*—About Dark Red 60A.
*Firmness.*—Firm; typically 10 lb pressure at harvest.
*Juice.*—Medium, able to squeeze free juice easily.
*Acidity.*—Medium; 0.47% titratable acidity.
*Sweetness.*—High; about 18% Brix at harvest.

*Adherence to stone*.—Adherent.

*Amount of fiber*.—Medium.

Fruit use: Fresh market.

Fruit shipping and keeping characteristics: Excellent storage and shipping quality for 6 weeks without shrivel or softening.

Stone:

*Stone freeness*.—Cling.

*Stone size*.—Size: Medium. Length: Approximately 28 mm. Diameter in line with suture plan: Approximately 18 mm. Diameter perpendicular to suture plane: Approximately 7 mm.

*Color*.—About Medium Greyed-Orange 170B when dried.

*Position of maximum diameter*.—Middle.

*Shape from lateral view*.—Medium elliptic.

*Shape from ventral view*.—Narrow elliptic.

*Shape from basal view*.—Narrow elliptic.

*Base shape*.—Nearly straight.

*Apex shape*.—Pointed.

*Stone ridges*.—Rounded throughout.

*Stone outgrowing keel*.—Partially developed.

*Ventrical edge*.—Thin with slight wing throughout.

*Dorsal edge*.—Narrow, shallow grooves throughout.

*Fibers*.—Not visible.

*Symmetry in lateral view*.—Symmetrical or slightly asymmetrical.

*Texture of lateral surface*.—Slightly rough.

*Width of stalk-end*.—Medium.

*Tendency to split*.—Rare.

What is claimed is:

1. A new and distinct variety of plum tree named 'Suplum63' as herein described and illustrated.

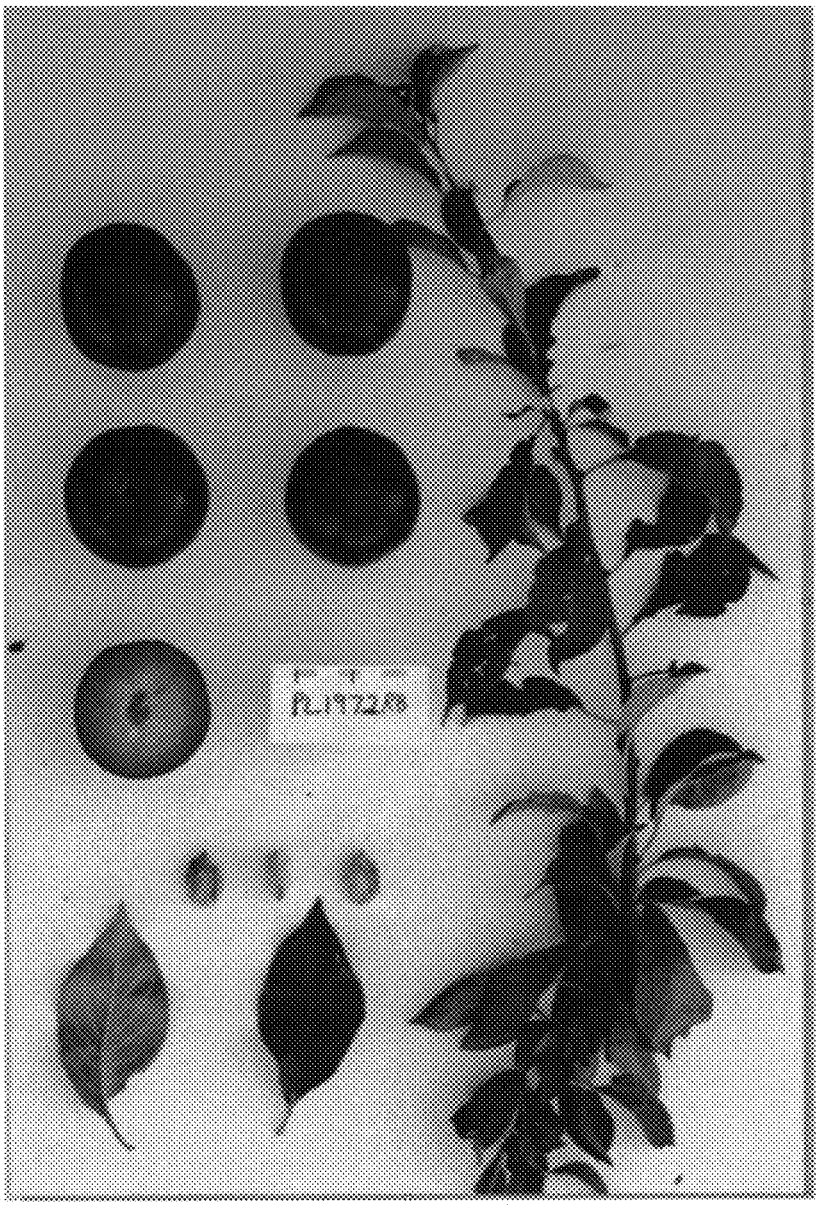

* * * * *